US010952936B2

(12) United States Patent
O'Connor et al.

(10) Patent No.: US 10,952,936 B2
(45) Date of Patent: Mar. 23, 2021

(54) CONCENTRATED POLYOLEFIN EMULSIONS AND PERSONAL CARE COMPOSITIONS CONTAINING THEM

(71) Applicants: Rohm and Haas Company, Collegeville, PA (US); Dow Global Technologies LLC, Midland, MI (US)

(72) Inventors: Ying O'Connor, Coatesville, PA (US); David L. Malotky, Midland, MI (US); Qichun Wan, Midland, MI (US); Rosalind Toth, King of Prussia, PA (US); Jodi A. Thomas, Midland, MI (US); Dale C. Schmidt, Midland, MI (US)

(73) Assignees: Dow Global Technologies LLC, Midland (ML); Rohm and Haas Company, Philadelphia, PA (US)

( * ) Notice: Subject to any disclaimer, the term of this patent is extended or adjusted under 35 U.S.C. 154(b) by 0 days.

(21) Appl. No.: 15/759,692

(22) PCT Filed: Nov. 14, 2016

(86) PCT No.: PCT/US2016/061791

§ 371 (c)(1),
(2) Date: Mar. 13, 2018

(87) PCT Pub. No.: WO2017/099946

PCT Pub. Date: Jun. 15, 2017

(65) Prior Publication Data

US 2019/0038527 A1 Feb. 7, 2019

Related U.S. Application Data

(60) Provisional application No. 62/266,254, filed on Dec. 11, 2015.

(51) Int. Cl.

| | |
|---|---|
| ***A61K 8/06*** | (2006.01) |
| ***A61K 8/81*** | (2006.01) |
| ***A61K 8/31*** | (2006.01) |
| ***A61Q 19/10*** | (2006.01) |
| ***A61K 8/44*** | (2006.01) |
| ***A61K 8/46*** | (2006.01) |
| ***A61Q 19/00*** | (2006.01) |

(52) U.S. Cl.
CPC .............. *A61K 8/062* (2013.01); *A61K 8/064* (2013.01); *A61K 8/31* (2013.01); *A61K 8/44* (2013.01); *A61K 8/463* (2013.01); *A61K 8/8111* (2013.01); *A61Q 19/00* (2013.01); *A61Q 19/10* (2013.01); *A61K 2800/48* (2013.01); *A61K 2800/54* (2013.01); *A61K 2800/805* (2013.01)

(58) Field of Classification Search
CPC .............................. A61K 8/062; A61K 8/8111
See application file for complete search history.

(56) References Cited

U.S. PATENT DOCUMENTS

| | | | | |
|---|---|---|---|---|
| 4,171,295 | A * | 10/1979 | Frese | C08L 95/005 524/501 |
| 4,568,713 | A * | 2/1986 | Hansen | C09J 123/20 524/291 |
| 4,701,432 | A | 10/1987 | Welborn, Jr. | |
| 5,272,236 | A | 12/1993 | Lai et al. | |
| 5,322,728 | A | 6/1994 | Davey et al. | |
| 5,539,021 | A | 7/1996 | Pate et al. | |
| 5,720,961 | A * | 2/1998 | Fowler | A61Q 5/02 424/401 |
| 6,525,157 | B2 | 2/2003 | Cozewith et al. | |
| 6,783,766 | B2 | 8/2004 | Pate et al. | |
| 6,897,247 | B2 | 5/2005 | Fredrickson | |
| 6,960,635 | B2 | 11/2005 | Stevens et al. | |
| 8,986,663 | B2 | 3/2015 | Jordan et al. | |
| 9,872,820 | B2 * | 1/2018 | O'Connor | A61Q 19/00 |
| 2002/0039565 | A1 * | 4/2002 | Aubrun-Sonneville | A61K 8/06 424/70.11 |
| 2005/0261417 | A1 | 11/2005 | Mezzenga et al. | |
| 2015/0224038 | A1 | 8/2015 | O'Connor et al. | |

FOREIGN PATENT DOCUMENTS

| | | |
|---|---|---|
| WO | 2015138210 A1 | 9/2015 |

OTHER PUBLICATIONS

Wikipedia: Polybutylene, 1 pg.*
Wikipedia, Polypropylene, 1 pg.*
Mechanical Properties of Polymers, https://www.smithersrapra.com/SmithersRapra/media/Sample-Chapters/Physical-Testing-of-Plastics.pdf, 140 pgs.*
Acumist A-45, 1 pgs, 2012.*

* cited by examiner

*Primary Examiner* — Kyle A Purdy
(74) *Attorney, Agent, or Firm* — Raef M. Shaltout

(57) ABSTRACT

Provided is a concentrated emulsion and personal care compositions containing the concentrated emulsion. The emulsion comprises: (a) from 60 to 95 wt %, based on the total weight of the emulsion, of an internal phase comprising: (i) a low density polyolefin with a density equal to or below 0.90 g/cm$^3$, and (ii) a cosmetically acceptable solvent; (b) from 0.1 to 30 wt %, based on the total weight of the emulsion, of a surfactant; and (c) balance water as a continuous phase.

9 Claims, No Drawings

CONCENTRATED POLYOLEFIN EMULSIONS AND PERSONAL CARE COMPOSITIONS CONTAINING THEM

FIELD

This invention relates generally to compositions that are useful as sensory agents in personal care products. The compositions contain a concentrated emulsion of a polyolefin.

BACKGROUND

Excellent sensory performance is highly desired in personal care compositions, including leave-on (lotion/cream, gel, sunscreens, color cosmetic), and rinse-off applications (body/face/hand wash, soap, shelving cream/gel). There is a consumer demand for products that deliver fast-spreading, non-oily, non-tacky, fast absorbing, products that also provide smooth and moisturizing after-feel in both applications.

The personal care art has developed sensory agents, such as silicone oils, hard particles (such as poly(methyl methacrylate) (PMMA) particles and polyethylene (PE) particles), and silicone elastomer gels in order to impart sensory benefits. However, each of the foregoing is associated with certain drawbacks, like insufficient sensory performance, poor conditioning, stability, and texture, or relatively high cost.

Even where a composition provides desirable performance, it may still be lacking based on how difficult it is to incorporate the composition in a personal care product. For instance, compositions that require high temperatures and strong agitation for processing, or high use amounts to achieve the desired performance, are still disadvantaged, for example because of the additional costs associated with their use.

Accordingly, there is a continuing need in the art for cost-effective, easily useable, high performance sensory agents for personal care products.

STATEMENT OF INVENTION

We have now found that polyolefins as described herein, which are highly effective sensory agents for personal care compositions, may be prepared as concentrated oil in water emulsions, for instance as high internal phase emulsions where the volume % internal phase is at least 75%. Advantageously, the emulsion is easily incorporated in personal care compositions at low concentrations and eliminates the need for high temperatures to melt the oil gel in the oil phase of such compositions.

In one aspect, therefore, there is provided a concentrated emulsion comprising:

(a) from 60 to 95 wt %, based on the total weight of the emulsion, of an internal phase comprising:
  (i) a low density polyolefin with a density equal to or below 0.90 g/cm$^3$, and
  (ii) a cosmetically acceptable solvent;
(b) from 0.1 to 30 wt %, based on the total weight of the emulsion, of a surfactant; and
(c) balance water as a continuous phase.

In another aspect, there is provided a personal care composition comprising: (a) a concentrated emulsion as described herein; and (b) a personal care additive.

In a further aspect, there is provided a method for preparing the concentrated emulsion according to the processes described herein.

In a still further aspect, there is provided a method for making a personal care composition containing a polyolefin and a personal care additive, the method comprising adding the polyolefin to the personal care composition in the form of the concentrated emulsion as described herein.

DETAILED DESCRIPTION

Unless otherwise indicated, numeric ranges, for instance as in "from 2 to 10," are inclusive of the numbers defining the range (e.g., 2 and 10). Unless otherwise indicated, ratios, percentages, parts, and the like are by weight. As used herein, unless otherwise indicated, the phrase "molecular weight" or Mw refers to the weight average molecular weight as measured in a conventional manner with gel permeation chromatography (GPC) and polyacrylic acid standards. GPC techniques are discussed in detail in Modem Size Exclusion Chromatography, W. W. Yau, J. J. Kirkland, D. D. Bly; Wiley-lnterscience, 1979, and in A Guide to Materials Characterization and Chemical Analysis, J. P. Sibilia; VCH, 1988, p. 81-84. Molecular weights are reported herein in units of Daltons. The term "polymer" refers to a polymeric compound prepared by polymerizing monomers, whether of the same or a different type. The generic term "polymer" includes the terms "homopolymer," "copolymer," and "terpolymer." An "olefin-based polymer" or "polyolefin" is a polymer that contains a majority mole percent polymerized olefin monomer (based on total amount of polymerizable monomers), and optionally, may contain at least one comonomer. Nonlimiting examples of olefin-based polymer include ethylene-based polymer and propylene-based polymer. Representative polyolefins include polyethylene, polypropylene, polybutene, polyisoprene and their various interpolymers. Weight percentages (or wt %) in the composition are percentages of dry or actives weight, i.e., excluding any water that may be present in the composition. Percentages of monomer units in the polymer are percentages of solids or neat monomer weight, i.e., excluding any water present in a polymer emulsion.

"Personal care" relates to compositions to be topically applied to a person (including mouth, ear, and nasal cavities, but not ingested) and include leave-on and rinse-off products. Examples of personal care compositions include skin care products (e.g., toners/serums/sprays/lotions/creams, gels, moisturizers, rinse off face/body/hand wash, shaving gels/lotions/creams, wipes, cleansing cloths, eye lotions/creams, sunscreens, foundation, blush, eye-shadow, primer, mascara, eye-liner, lipstick, cleansers, antiperspirants, deodorants, and the like). Preferably, the personal care composition is a skin care composition. Preferably, the personal care composition is a rinse-off product, more preferably a rinse-off skin care composition. "Cosmetically acceptable" refers to ingredients typically used in personal care compositions, and is intended to underscore that materials that are toxic when present in the amounts typically found in personal care compositions are not contemplated as part of the present invention.

As noted above, in one aspect, the invention provides a concentrated emulsion. The concentrated emulsion is comprised of from 60 to 95 wt % of an internal phase that contains a low density polyolefin with a density (as measured by ASTM D 792) equal to or below 0.90 g/cm$^3$, preferably from 0.86 to 0.90 g/cm$^3$, and a cosmetically acceptable solvent. In certain preferred embodiments, the concentrated emulsion comprises 60 to 95 wt % of an internal phase that contains a high density polyolefin with a density above 0.90 g/cm$^3$, a low density polyolefin with a density equal to or below 0.90 g/cm$^3$, preferably from 0.86 to 0.90 g/cm$^3$, and a cosmetically acceptable solvent.

In certain embodiments, when both a high and a low density polyolefin are present in the internal phase, the average melt index (g/10 min, as measured by ASTM D 1238) for the high and low density polyolefins is greater than 7, preferably greater than 8, and more preferably greater than 8.5.

In certain embodiments, the high density polyolefin has a weight-average molecular weight in a range of from 41,000 to 500,000, preferably 70,000 to 90,000, and more preferably from 75,000 to 85,000. In certain embodiments, the low density polyolefin, when present, has a weight-average molecular weight in a range of from 5,000 to 40,000, preferably 10,000 to 30,000, and more preferably from 20,000 to 28,000. In certain preferred embodiments the concentrated emulsion is substantially free of ethylene-acrylic acid copolymer.

High and low density polyolefins for use in the invention are produced with a metallocene catalyst. Metallocene catalysis enables control of the polyolefin properties relating to, for example, crystallinity, polymer chain length, and distribution homogeneity of the polymer chain units. Metallocene catalysis also favors uniformity in polymer chains density and length. Suitable metallocene catalysts include, for example, those described in U.S. Pat. Nos. 4,701,432, 5,322,728, and 5,272,236. In certain embodiments of the present invention, the polyolefins are polyethylenes produced with a metallocene catalyst. Suitable polyethylenes are available from, for example, The Dow Chemical Company under the trademark AFFINITY or ENGAGE (ethylene/octene copolymers), and from Exxon Chemical Company under the trademark EXACT (ethylene/butene copolymers, ethylene/hexene copolymers, or ethylene/butene/hexene terpolymers). In one embodiment, the low density polyolefin and, when present, the high density polyolefin, are independently at least one of ethylene/octene copolymers, ethylene/butene copolymers, ethylene/hexene copolymers, ethylene/propylene or ethylene/butene/hexene terpolymers, preferably an ethylene octene copolymer. In another embodiment, the low density polyolefin and, when present, the high density polyolefin, are independently a propylene/alpha-olefin copolymer. Suitable propylene/alpha-olefin copolymers include, for example, those described in detail in U.S. Pat. Nos. 6,960,635 and 6,525,157. Such propylene/alpha-olefin copolymers are commercially available from The Dow Chemical Company under the trademark VERSIFY, or from ExxonMobil Chemical Company under the trademark VISTAMAXX. Other suitable polyolefins are sold by The Dow Chemical Company under the trademarks AMPLIFY, ATTANE, INFUSE, NORDEL, and VLDPE. Other suitable non-limiting examples of commercially available metallocene catalyzed polyethylenes and the melt index and density of each is as shown in Table 1.

TABLE 1

Specified Metallocene Catalyzed Polyethylenes

| Polyolefin Name | Melt Index | Density |
|---|---|---|
| AFFINITY GA1000R | 600 | 0.878 |
| AFFINITY GA 1950 | 500 | 0.874 |
| AFFINITY PL1840G | 1 | 0.909 |
| AMPLIFY EA 103 | 21 | 0.930 |
| AMPLIFY GR 202 | 8 | 0.930 |
| AMPLIFY GR 204 | 12.0 | 0.953 |
| AMPLIFY GR 216 | 1.25 | 0.870 |

TABLE 1-continued

Specified Metallocene Catalyzed Polyethylenes

| Polyolefin Name | Melt Index | Density |
|---|---|---|
| ATTANE 4203 | 0.8 | 0.905 |
| ATTANE 4404G | 4 | 0.904 |
| ENGAGE 8100 | 1 | 0.870 |
| ENGAGE 8130 | 13 | 0.863 |
| ENGAGE 8200 | 5 | 0.870 |
| ENGAGE 8402 | 30 | 0.902 |
| INFUSE D9807 | 15 | 0.866 |
| LDPE 4016 | 16 | 0.916 |
| LDPE 640I | 2 | 0.920 |
| LDPE 955I | 35 | 0.923 |
| VERSIFY 2200 | 2 | 0.876 |
| VERSIFY 3200 | 8 | 0.876 |
| VERSIFY 4200 | 25 | 0.876 |

Both low and high density polyolefins may independently contain optional functional groups. Such a functional group may enhance deposition or attachment of the polymer to skin. The functional groups are grafted onto a polyolefin by any suitable means known in the prior art. The functional group may also be incorporated through copolymerization of a suitable monomer containing the desired functional group. Examples of suitable functional groups include one or more groups independently selected from hydroxyl, phosphono, acid anhydride, amino, epoxy, sulfate, sulfonate, amido, silanes, and ester groups.

In an embodiment, the functionalized low or high density polyolefin (or both) in the composition of the invention is selected from an anhydride-functionalized polyolefin, a acrylate or methacrylate functionalized polyolefin, a silane functionalized polyolefin, and combinations thereof. In an embodiment, the low or high density functionalized polyolefin is selected from anhydride-functionalized polyolefin, a silane-functionalized polyolefin and combinations thereof.

In an embodiment, the low or high density functionalized polyolefin is a maleic-anhydride-functionalized polyolefin. In a further embodiment, the low or high density functionalized polyolefin is a maleic-anhydride functionalized ethylene/α-olefin interpolymer. In a further embodiment, the low or high density functionalized polyolefin is a maleic-anhydride functionalized ethylene/octene interpolymer.

Nonlimiting examples of functionalized polyolefins include maleic anhydride (MAH)-grafted copolymers (for example, AFFINITY™ GA 1000R Polyolefin Plastomer and AMPLIFY™ GR 216 Polyolefin Elastomer, available from The Dow Chemical Company).

In certain preferred embodiments the inventive compositions described herein are substantially free of EAA. "Substantially free" in this context means less than 3 weight %, preferably less than 1 weight %, more preferably less than 0.1 weight %, and even more preferably zero weight percent present in the composition.

In one embodiment, the internal phase comprises the low density polyolefin which is present in an amount ranging from 5 to 30 weight %, preferably from 5 to 15 weight %, of solids by weight of the internal phase. In one embodiment, the internal phase comprises the low density polyolefin which is present in an amount ranging from 10 to 30 weight %, preferably from 15 to 25 weight %, of solids by weight of the internal phase.

In one embodiment, the internal phase comprises from 5 to 30 weight % of the low density polyolefin and from 0 to 30 weight % of a high density polyolefin, preferably from 2 to 16 weight %, of solids by weight of the internal phase. In one embodiment, a high density polyolefin is present and the ratio of polyolefin with a density above 0.90 g/$cm^3$ to the polyolefin with a density equal to or below 0.90 g/$cm^3$ is between 1:95 and 95:1, preferably between 10:50 and 60:10, and more preferably between 10:40 and 40:10. In certain preferred embodiments, the ratio is 1:1, 1.5:1, 2:1, or 3:1.

A variety of cosmetically acceptable solvents may be used in the internal phase. Such solvents are generally water immiscible. Examples include, without limitation, hydrocarbon solvents, ester solvents, silicone oil solvents, or mixtures thereof. Preferably, the cosmetically acceptable solvent comprises a cosmetically acceptable hydrocarbon oil.

Cosmetically acceptable hydrocarbon oils suitable for use in the present invention may be selected from various carbon chain length oils. In certain embodiments, the hydrocarbon oils include, but are not limited to, $C_{14}$-$C_{22}$ hydrocarbon oils. In certain embodiments, the hydrocarbon oil is less than fourteen carbons in length. In certain embodiments, the hydrocarbon oil is greater than twenty-two carbons in length. Suitable hydrocarbon oils include, for example, those sold under the trademarks LILAC, GEMSEAL 25, GEMSEAL 40, PERMETHYL 101A, PERMETHYL 99A, SILKFLO 364 NF, SILKFLO 366 NF, FANCOL POLYISO 200-CG, FANCOL POLYISO 300-CG, FANCOL POLYISO 450-CG, FANCOL POLYISO 800-CG, PANALANE L-14E, PURESYN 2, PURESYN 4, or RITADECENE 20. A preferred hydrocarbon oil is Lilac white oil. In certain embodiments, the cosmetically acceptable solvent is present in an amount of from 35 to 90 weight %, preferably 65 to 85 weight %, by weight of the internal phase.

The concentrated emulsion contains a surfactant. The surfactant may be cationic, nonionic, anionic, amphoteric, or combinations thereof. The surfactant is typically present in the concentrated emulsion in an amount ranging from 0.1 to 30 wt %, preferably 0.1 to 25 wt %, preferably 1 to 15 wt %, more preferably 2 to 8 wt %, by weight of the concentrated emulsion.

Cationic surfactants suitable for use in the concentrated emulsion include, for example, quaternary ammonium salt surfactants. Suitable quaternary ammonium salt surfactants include, for instance, dialkyldimethylammonium salt surfactants, alkylbenzyldimethyl-ammonium salt surfactants, alkyltrimethylammonium salt surfactants, and alkylpyridinium halide surfactants. Suitable quaternary ammonium salt surfactants have corresponding anions. Suitable corresponding anions include, for example, halide ions (such as, for example, chloride ions), methyl sulfate ions, other anions, and mixtures thereof. Specific examples of cationic surfactants include, without limitation, behenyltrimethylammonium chloride, or cetrimonium chloride. Cetrimonium chloride is preferred. Mixtures of cationic surfactants may be used.

Anionic surfactants that may suitable by used in the concentrated emulsion include, without limitation, C11-C18 alkyl benzene sulfonates and primary or branched-chain C10-C20 alkyl sulfates, unsaturated sulfates such as oleyl sulfate, the C10-C18 alkyl alkoxy sulfates, particularly those comprising 1-7 ethoxy groups, C10-C18 alkyl alkoxy carboxylates, particularly those comprising 1-5 ethoxy groups, the C10-C18 glycerol ethers, the C10-C18 alkyl polyglycosides and their corresponding sulfated polyglycosides, and C12-C18 alpha-sulfonated fatty acid esters. Other useful anionic surfactants include water-soluble salts, particularly the alkali metal, ammonium and alkylolammonium salts, such as monoethanolammonium or triethanolammonium salts, of organic sulfuric reaction products having in their molecular structure an alkyl group containing from about 10 to about 20 carbon atoms and a sulfonic acid or sulfuric acid ester group. Other anionic surfactants useful herein are the water-soluble salts of alkyl phenol ethylene oxide ether sulfates and water-soluble salts of esters of alpha-sulfonated fatty acids. Anionic surfactants based on fatty acids may be used and include saturated and/or unsaturated fatty acids obtained from natural sources or synthetically prepared. Examples of suitable fatty acids include, but are not limited to, capric, lauric, myristic, palmitic, stearic, arachidic, and behenic acid. Other fatty acids include palmitoleic, oleic, linoleic, linolenic, and ricinoleic acid. Examples of particularly preferred surfactants are fatty acid salts, sulfonates or quaternary ammonium salts, and especially sodium lauryl sulfate (SLS) or sodium laureth sulfate (SLES).

Nonionic surfactants that may be used in the concentrated emulsion of the invention include, for example, polyoxyalkylene surfactants, polyalkylene glycol esters, polyoxyethylene derivatives of fatty acid esters of polyhydric alcohols, fatty acid esters of polyalkoxylated polyhydric alcohols, polyalkoxylated natural fats and oils, polyalkylene oxide block copolymers, alkyl polyglucosides, sucrose esters, and mixtures thereof. Among the suitable polyoxyalkylene surfactants, some suitable examples are polyoxyethylene surfactants, including, for example, alcohol alkoxylates, alkylphenol alkoxylates, and mixtures thereof. Suitable alcohol alkoxylates include, for example, alcohol ethoxylates and alcohol propoxylates. In some embodiments, one or more alcohol ethoxylate is used. Specific examples of nonionic surfactants include, without limitation, laureth-23, ceteth-20, steareth-100, or coco glucoside.

The concentrated emulsion of the invention contains water as a continuous phase. The water generally comprises the balance of the concentrated emulsion, to bring the emulsion to 100%, after the amounts of the other ingredients have been selected. In some embodiments, the amount of water in the emulsion is at least 5 wt %, alternatively at least 10 wt %, and up to 40 wt %, alternatively up to 30 wt %, by weight of the concentrated emulsion. As is apparent, the emulsion of the invention contains the internal, oil phase, at a high concentration. In some embodiments, the concentrated emulsion may be considered a high internal phase emulsion (HIPE) containing, for instance, at least 75 wt % of the internal phase, by weight of the emulsion.

The emulsion of the invention may contain optional ingredients, including additional surfactants, such as zwitterionic surfactants, and preservatives such as benzoic acid, sorbic acid, or phenoxyethanol.

The concentrated emulsion may be prepared by a variety of methods, including batch and continuous methods well known in the art. In a preferred continuous method (described generally by Pate et al in U.S. Pat. No. 5,539,021, column 3, line 15 to column 6, line 27, which is incorporated herein by reference), a stream containing the continuous aqueous phase is flowed through a first conduit and merged continuously with a stream of the disperse internal phase that is flowed through a second conduit. The streams are merged into a disperser in the presence of one or more surfactants. The surfactants can be added to either stream, or as a separate stream. Additional details can be found, for instance, in U.S. Pat. No. 6,783,766, which is incorporated herein by reference.

In another aspect, the invention provides a personal care composition comprising a concentrated emulsion as described above and a personal care additive. In certain embodiments, the concentrated emulsion is present in an amount of from 0.01 to 50 weight %, preferably 1 to 10 weight %, and more preferably 2 to 5 weight %, by weight of the personal care composition.

Examples of personal care additives that may suitably be used in the composition include, without limitation, one or more of: an emollient, an emulsifier and/or a surfactant, a thickener, a carrier, an active ingredient, or a sunscreen.

An emollient suitable for use in the invention may be at least one of a moisturizer, a conditioner, oil, or other fatty substance. For example, when the personal care composition is in an emulsion form, it comprises at least one oily phase that contains at least one oil, especially a cosmetically acceptable oil. The term "oil" means a fatty substance that is liquid at room temperature. Examples of oils include hydrocarbon-based oils of animal origin, such as squalene, hydrocarbon-based oils of plant origin, such as liquid triglycerides of fatty acids comprising from 4 to 10 carbon atoms, for instance heptanoic or octanoic acid triglycerides, or alternatively, oils of plant origin, for example sunflower oil, corn oil, soybean oil, marrow oil, grapeseed oil, sesame seed oil, hazelnut oil, apricot oil, macadamia oil, arara oil, coriander oil, castor oil, avocado oil, jojoba oil, shea butter oil, or caprylic/capric acid triglycerides, MIGLYOL 810, 812 and 818 (from Dynamit Nobel), synthetic or natural esters and ethers, especially of fatty acids, for instance the oils of formulae $R^1COOR^2$ and $R^1OR^2$ in which IV represents a fatty acid residue comprising from 8 to 29 carbon atoms and $R^2$ represents a branched or unbranched hydrocarbon-based chain comprising from 3 to 30 carbon atoms, for instance purcellin oil, isononyl isononanoate, isopropyl myristate, 2-ethylhexyl palmitate, 2-octyldodecyl stearate, 2-octyldodecyl erucate or isostearyl isostearate, hydroxylated esters, for instance isostearyl lactate, octyl hydroxystearate, octyldodecyl hydroxystearate, diisostearyl malate, triisocetyl citrate and fatty alcohol heptanoates, octanoates and decanoates, polyol esters, for instance propylene glycol dioctanoate, neopentyl glycol diheptanoate and diethylene glycol diisononanoate, pentaerythritol esters, for instance pentaerythrityl tetraisostearate, lipophilic derivatives of amino acids, such as isopropyl lauroyl sarcosinate, such as is sold under the name ELDEW SL 205 (from Ajinomoto), linear or branched hydrocarbons of mineral or synthetic origin, such as mineral oils (mixtures of petroleum-derived hydrocarbon-based oils), volatile or non-volatile liquid paraffins, and derivatives thereof, petroleum jelly, polydecenes, isohexadecane, isododecane, hydrogenated isoparaffin (or polyisobutene), silicone oils, for instance volatile or non-volatile polymethylsiloxanes (PDMS) comprising a linear or cyclic silicone chain, which are liquid or pasty at room temperature, especially cyclopolydimethylsiloxanes (cyclomethicones) such as cyclopentasiloxane and cyclohexadimethylsiloxane, polydimethylsiloxanes comprising alkyl, alkoxy or phenyl groups, which are pendent or at the end of a silicone chain, these groups comprising from 2 to 24 carbon atoms, phenyl silicones, for instance phenyl trimethicones, phenyl dimethicones, phenyltrimethylsiloxydiphenylsiloxanes, diphenyl dimethicones, diphenylmethyldiphenyltrisiloxanes 2-phenylethyltrimethyl siloxysilicates and polymethylphenylsiloxanes, fluoro oils such as partially hydrocarbon-based and/or partially silicone-based fluoro oils, ethers such as dicaprylyl ether (CTFA name: dicaprylyl ether), and $C_{12}$-$C_{15}$ fatty alcohol benzoates (FINSOLV TN from Finetex), mixtures thereof.

Oils include mineral oil, lanolin oil, coconut oil and derivatives thereof, cocoa butter, olive oil, almond oil, macadamia nut oil, aloe extracts such as aloe vera lipoquinone, jojoba oils, safflower oil, corn oil, liquid lanolin, cottonseed oil, peanut oil, hydrogenated vegetable oil, squalane, castor oil, polybutene, sweet almond oil, avocado oil, calophyllum oil, ricin oil, vitamin E acetate, olive oil, silicone oils such as dimethylopolysiloxane and cyclomethicone, linolenic alcohol, oleyl alcohol, and the oil of cereal germs.

Other suitable emollients include dicaprylyl ether, $C_{12-15}$ alkyl benzoate, DC 200 FLUID 350 silicone fluid (from Dow Corning Corp.), isopropyl palmitate, octyl palmitate, isopropyl myristate, hexadecyl stearate, butyl stearate, decyl oleate, acetyl glycerides, the octanoates and benzoates of $C_{12-15}$ alcohols, the octanoates and decanoates of alcohols and polyalcohols such as those of glycol and glyceryl, ricinoleates esters such as isopropyl adipate, hexyl laurate and octyl dodecanoate, dicaprylyl maleate, phenyltrimethicone, and aloe vera extract. Solid or semi-solid cosmetic emollients include glyceryl dilaurate, hydrogenated lanolin, hydroxylated lanolin, acetylated lanolin, petrolatum, isopropyl lanolate, butyl myristate, cetyl myristate, myristyl myristate, myristyl lactate, shea butter, coconut butter, bee waxes, or any natural butters/waxes, cetyl alcohol, isostearyl alcohol and isocetyl lanolate.

In one embodiment, the emollient is present in an amount from 0.05% to 40% by weight of the personal care composition. Preferably, the emollient is present in an amount from 0.1% to 10% by weight of the composition.

Emulsifiers and surfactants suitable for use in the personal care compositions may be selected from amphoteric, anionic, cationic and nonionic emulsifiers or surfactants, used alone or as a mixture. Anionic surfactants include soaps or salts of fatty acids, alkyl sulfates, alkyl ether sulfates, alpha-olefin sulfonates, alkyl aryl sulfonates, sarcosinates, alkyl glucose esters or their alkoxylates, and in particular sodium lauryl sulfate, ammonium lauryl sulfate, triethanolamine lauryl sulfate, sodium laureth sulfate, isethionates, and triethanolamine stearate. Nonionic surfactants include methyl glucose stearates or their ethoxylates, alkyl polyglucosides, and glycerol monostearate, sucrose esters, fatty acid alkanol amides, alkyl aryl polyglycol ether, polyglycol ethers and in particular cocoyl diethanolamide, nonoxynol-7 and octoxynol-9; cationics including alkyl trimethyl ammonium salts, quaternized amides of ethylene diamine, alkyl pyridinium salts and in particular cetrimonium chloride, stearalkonium chloride and cetyl pyridinium chloride; and amphoterics including alkyl .beta.-aminopropionates, betaines, alkyl imidazolines and in particular cocamidopropyl betaine and caproam phocarboxy propionate. Polymeric cationic emulsifiers that include hydrophobic moieties are preferred, examples of which include polyquaternium-10 (UCARE™), polyquaternium-24 and polyquaternium 67 (SOFTCAT™), available from The Dow Chemical Company, and guar hydroxypropyltrimonium chloride.

Emulsions free of emulsifying surfactants or comprising less than 0.5% of emulsifying surfactants relative to the total weight of the composition may also be prepared, by using suitable compounds, for example polymers having emulsifying properties, such as CARBOPOL 1342 polymer (Noveon), PEMULEN polymer (Noveon), SEPIGEL 305 polyacrylamide/C13-C14 isoparaffin/laureth-7 (Seppic), particles of ionic or nonionic polymers, particles of anionic polymer such as, isophthalic acid, sulfoisophthalic acid polymers, and phthalate/sulfoisophthalate/glycol copolymers (for example diethylene glycol/phthalate/isophthalate/1,4-cyclohexanedimethanol sold under the names Eastman AQ diglycol/CHDM/isophthalates/SIP copolymer (AQ35S, AQ38S, AQ55S and/or AQ48 Ultra, from Eastman Chemical). Emulsifier-free emulsions stabilized with silicone particles or metal oxide particles such as $TiO_2$ or the like may also be prepared.

The emulsifier or surfactant may be present in an amount from 0.01% to 40% by weight of the personal care composition. In one embodiment, the surfactant is present in an amount from 0.1% to 12% by weight of the composition.

Examples of thickeners that may be used in the personal care compositions of the invention include polymers, for example, modified or unmodified carboxyvinyl polymers, such as the products sold under the names CARBOPOL and PEMULEN (INCI name: Acrylates/C10-30 alkyl acrylate crosspolymer; available from Noveon), polyacrylates and polymethacrylates, such as the products sold under the names LUBRAJEL and NORGEL (from Guardian) or HISPAGEL (from Hispano Chimica), polyacrylamides, 2-acrylamido-2-methylpropanesulfonic acid polymers and copolymers, which are optionally crosslinked and/or neutralized, for instance the poly(2-acrylamido-2-methylpropane-sulfonic acid) sold by Clariant (INCI name: ammonium polyacryldimethyltauramide), emulsified crosslinked anionic copolymers of acrylamide and AMPS, such as those sold under the name SEPIGEL 305 (INCI name: Polyacrylamide/C13-14 Isoparaffin/Laureth-7; from Seppic) and under the name SIMULGEL 600 (INCI name: Acrylamide/Sodium acryloyldimethyltaurate copolymer/Isohexadecane/Polysorbate 80; from Seppic), polysaccharide biopolymers, for instance xanthan gum, guar gum, carob gum, acacia gum, scleroglucans, chitin and chitosan derivatives, carrageenans, gellans, alginates, celluloses such as microcrystalline cellulose, carboxymethylcellulose, hydroxymethylcellulose and hydroxypropylcellulose, associative polymers, for instance associative polyurethanes, copolymers comprising at least two hydrocarbon-based lipophilic chains comprising from 6 to 30 carbon atoms, separated with a hydrophilic sequence, such as the polyurethanes sold under the names SERAD FX1010, SERAD FX1100 and SERAD FX1035 (from Hüls America), RHEOLATE 255, RHEOLATE 278 and RHEOLATE 244 (INCI name: Polyether-urea-polyurethane; from Rheox), DW 1206F, DW 1206J, DW 1206B, DW 1206G, and ACRYSOL RM 2020 (from Rohm & Haas). Some preferred thickeners are Aculyn thickeners (INCI name: Acrylates Copolymer) and METHOCEL hydroxypropyl methylcellulose, available from The Dow Chemical Company.

In one embodiment, the thickener is present in an amount from 0.01% to 10% by weight of the personal care composition. In one embodiment, the thickener is present in an amount from 0.1% to 5% by weight of the composition.

The personal care composition preferably comprises a suitable carrier, or mixtures of carriers. The type of carrier depends on the particular end use of the composition. Illustrative carriers include, for example, water, such as deionized or distilled water, emulsions, such as oil-in-water or water-in-oil emulsions, alcohols, such as ethanol, isopropanol or the like, glycols, such as propylene glycol, glycerine or the like, or combinations thereof. A preferred carrier is deionized water.

Active ingredients that may be present in the personal care composition of the invention include skin care actives or nail care actives. Actives include sunscreens, skin colorants, drug substances (such as anti-inflammatory agents, antibiotics, topical anesthetics, antimycotics, keratolytics, and the like), anti-oxidants, anti-aging ingredients, vitamins, natural extracts, skin protectants, conditioners, moisturizers, humectants, and ultraviolet radiation absorbers.

Examples of sunscreens include para aminobenzoic acid, avobenzone, cinoxate, dioxybenzone, homosalate, menthyl anthranilate, octocrylene, octyl methoxycinnamate, octyl salicylate, oxybenzone, padimate 0, phenylbenzimidazole sulfonic acid, sulisobenzone, trolamine salicylate, titanium dioxide, zinc oxide, benzophenones, benzylidenes, salicylates, or other known UV filters, including diethanolamine methoxycinnamate, digalloy trioleate, ethyl dihydroxypropyl PABA, glyceryl aminobenzoate, and lawsone with dihydroxy acetone and red petrolatum.

The personal care compositions of the invention may contain other optional ingredients including any suitable substance for personal care compositions, for example, colorants, preservatives, pH adjustors, reducing agents, fragrances, foaming agents, tanning agents, depilatory agents, astringents, antiseptics, deodorants, antiperspirants, insect repellants, and biocides.

Colorants include pigments, which are used especially in make-up, including metal oxide pigments, titanium dioxide, optionally surface-treated, zirconium oxide or cerium oxide, zinc oxide, iron oxide (black, yellow or red), chromium oxide, manganese violet, ultramarine blue, chromium hydrate and ferric blue, carbon black, pigments of barium, strontium, calcium or aluminum (for example D&C or FD&C), cochineal carmine, mica coated with titanium or with bismuth oxychloride, titanium mica with iron oxides, titanium mica with, especially, ferric blue or chromium oxide, titanium mica with an organic pigment, nacreous pigments based on bismuth oxychloride, goniochromatic pigments, for example pigments with a multilayer interference structure, reflective pigments, for example particles with a silver-coated glass substrate, glass substrate coated with nickel/chromium/molybdenum alloy, glass substrate coated with brown iron oxide, particles comprising a stack of at least two polymer layers, for instance MIRROR GLITTER (from 3M).

Dyes include water-soluble dyes such as copper sulfate, iron sulfate, water-soluble sulfopolyesters, rhodamines, natural dyes, for instance carotene and beetroot juice, methylene blue, caramel, the disodium salt of tartrazine and the disodium salt of fuschin, and mixtures thereof. Liposoluble dyes may also optionally be used.

Preservatives include alcohols, aldehydes, methylchloroisothiazolinone and methylisothiazolinone, p-hydroxybenzoates, potassium sorbate, sodium benzoate, and in particular methylparaben, propylparaben, glutaraldehyde and ethyl alcohol.

Suitable pH adjustors, include inorganic and organic acids and bases and in particular aqueous ammonia, citric acid, phosphoric acid, acetic acid, sodium hydroxide, potassium hydroxide, and triethanolamine. In a preferred embodiment, the pH adjustor is aminomethyl propanol, L-arginine, tromethamine, PEG-15 cocamine, diisopropanolamine, triisopropanolamine, or tetrahydroxypropyl ethylenediamine. In a particularly preferred embodiment, the pH adjustor is amino methyl propanol, Aminomethyl propanol is available under the tradename AMP-ULTRA from Angus Chemical Company. In one embodiment, the pH adjustor is present in an amount from 0.01% to 1% by weight of the composition. In one embodiment, the pH adjustor is present in an amount from 0.1% to 0.5% by weight of the composition.

Reducing agents include ammonium thioglycolate, hydroquinone and sodium thioglycolate.

Fragrances include any component which provides a pleasant scent. Fragrances are generally aldehydes or ketones, and often oils obtained by extraction of natural substances or synthetically produced. Often, fragrances are accompanied by auxiliary materials, such as fixatives, extenders, stabilizers and solvents.

Biocides include antimicrobials, bactericides, fungicides, algaecides, mildicides, disinfectants, antiseptics, and insecticides.

In some preferred embodiments, the personal care additive comprises: a carrier, an emollient, a thickener, and a preservative.

The amount of optional ingredients effective for achieving the desired property provided by such ingredients can be readily determined by one skilled in the art. Personal care compositions of the invention may generally be prepared by creating the formulation in the manner appropriate for the desired end-use. Such methods are well known to those skilled in the art.

In use, the personal care compositions are applied in a conventional manner.

Some embodiments of the invention will now be described in detail in the following Examples.

EXAMPLES

Example 1. Preparation of Polymer Blend Olefin Gel and Concentrated Emulsion A polyolefin gel was synthesized in an oil jacketed five gallon batch mixer (Model #VME-12 available from Fryma Maschinen AG, Switzerland) equipped with a sweep mixing blade. The mixer was loaded with 4788 g of isohexadecane (Permethyl 101A from Presperse) and the sweep mixing blade was turned on at a speed of 60 rpm. 456 g each of AFFINITY PL1840G and AFFINITY GA1950 were weighed out and blended together. This blend was slowly added to the mixing isohexadecane, after which the oil jacket was used to heat the mixture to an internal temperature of 117° C. under continued mixing. This heat up step took 100 minutes. Once the material reached the target temperature for 117° C., mixing was continued for an additional 60 minutes, after which the oil jacket temperature setpoint was reduced to 66° C., causing the mixture to cool down under continued mixing. After an additional 150 minutes the internal temperature of the mixer had dropped below 70° C. and the olefin gel was unloaded from the mixer for later use.

This olefin gel was loaded into a Nordson Altablue 4TT hot melter where the reservoir and delivery line have both been set to 110° C. The olefin gel was then pumped at a rate of 20.7 g/min into a two inch diameter rotor stator mixer heated to 110° C. and spinning at 1050 rpm. The internal phase was merged at the mixer with a separate deionized water stream flowing at 1.0 ml/min and a second aqueous stream of 50% active coco glucoside flowing at 1.6 ml/min. Both aqueous streams were fed by 500 ml Isco syringe pumps. The resultant polyolefin gel emulsion has a volume mean particle size of 1.4 microns. The olefin gel emulsion then passed through an exit tubing set to 90° C. and a backpressure regulator set to 50 psi, which keeps the water in the process liquid at all times.

Example 2: Preparation of Single Polymer Olefin Gel and Concentrated Emulsion A polyolefin gel was synthesized in a one gallon glass jar. The jar was loaded with 1208 g of isohexadecane (Permethyl 101A from Presperse) and 230 g of INFUSE™ D9807 and then placed in an oven at 90° C. overnight. This caused the polymer pellets to swell with the solvent, but they still maintained their shape. The oven temperature was then increased to 120° C. for one hour to completely melt the INFUSE D9807 and generate a clear uniform phase.

This uniform phase was loaded into a Nordson Altablue 4TT hot melter where the reservoir and delivery line have both been set to 110° C. The olefin gel was then pumped at a rate of 15 g/min into a two inch diameter rotor stator mixer heated to 120° C. and spinning at 850 rpm. The internal phase was merged at the mixer with a separate deionized water stream flowing at 0.9 ml/min and a second aqueous stream of 70% active sodium laureth sulfate (EMPICOL ESB) flowing at 0.9 ml/min. Both aqueous streams were fed by 500 ml Isco syringe pumps. The resultant polyolefin gel emulsion has a volume mean particle size of 0.5 microns and flowed into a second two inch diameter rotor stator mixer heated to 120° C. and spinning at 450 rpm where it was combined with an additional deionized water stream flowing at 3 ml/min to dilute the concentrated emulsion down to 75.8% internal phase. The concentrated emulsion then passed through an exit tubing set to 90° C. and a backpressure regulator set to 50 psi, which keeps the water in the process liquid at all times.

Example 3: Preparation of Single Polymer Olefin Gel and Concentrated Emulsion from a Functional Polymer A polyolefin gel was synthesized in a one gallon glass jar. The jar was loaded with 1200 g of C14-22-alkane (LILAC from Sonneborn) and 300 g of AFFINITY™ GA1000R (a maleic anhydride (MAH)-grafted copolymer) and then placed in an oven at 105° C. overnight. This caused the polymer pellets to melt and become partially dissolved. The phase was then mixed with a 2 inch diameter propeller mixer at 1200 rpm until the polymer was completely dissolved (5 minutes) to generate a clear uniform phase.

This uniform phase was loaded into a Nordson Altablue 4TT hot melter where the reservoir and delivery line have both been set to 100° C. The olefin gel was then pumped at a rate of 16.4 g/min into a two inch diameter rotor stator mixer heated to 100° C. and spinning at 1050 rpm. The internal phase was merged at the mixer with a separate deionized water stream flowing at 1.2 ml/min and a second aqueous stream of 50% active coco glucoside flowing at 1.45 ml/min. Both aqueous streams were fed by 500 ml Isco syringe pumps. The resultant polyolefin gel emulsion has a volume mean particle size of 3.1 microns and flowed into a second two inch diameter rotor stator mixer heated to 100° C. and spinning at 450 rpm where it was combined with an additional deionized water stream flowing at 2 ml/min to dilute the concentrated emulsion down to 77.9% internal phase. The concentrated emulsion then passed through an exit tubing set to 90° C. and a backpressure regulator set to 50 psi, which keeps the water in the process liquid at all times.

Example 4: Preparation of a Single Polymer Olefin Gel and Concentrated Emulsion from a Low Melt Flow Polymer A polyolefin gel was synthesized in a 4CV helicone mixer. The mixer was loaded with 1408 g of C14-22-alkane (LILAC from Sonneborn), which was heated to an internal temperature of 110° C. At this point the mixer was turned on at 75 rpm and 192 g of ENGAGE 8200 was loaded into the mixer and mixing was allowed to continue for 2 hours.

This uniform phase was loaded into a Nordson Altablue 4TT hot melter where the reservoir and delivery line have both been set to 110° C. The olefin gel was then pumped at a rate of 17.1 g/min into a two inch diameter rotor stator mixer heated to 110° C. and spinning at 1050 rpm. The internal phase was merged at the mixer with a separate deionized water stream flowing at 1.0 ml/min and a second aqueous stream of 50% active coco glucoside flowing at 1.5 ml/min. Both aqueous streams were fed by 500 ml Isco syringe pumps. The resultant polyolefin gel emulsion has a volume mean particle size of 2.1 microns and flowed into a second two inch diameter rotor stator mixer heated to 110° C. and spinning at 450 rpm where it was combined with an additional deionized water stream flowing at 2 ml/min to dilute the concentrated emulsion down to 79.2% internal phase. The concentrated emulsion then passed through an exit tubing set to 90° C. and a backpressure regulator set to 50 psi, which keeps the water in the process liquid at all times.

Examples 5. Body Wash Formulation

Materials Tested in this Example:

PO HIPE: the inventive concentrated emulsion of Example 1

PO Gel: a comparative polyolefin oil gel that is not in the form of a concentrated emulsion. The PO Gel contains a low density polyolefin (Affinity GA 1950), a high density polyolefin (Affinity PL 1840G), and a carrier that is Lilac (C14~22 Alkane).

In this example, PO HIPE is compared against PO Gel in a body wash formulation.

A standard body wash formulation is prepared by using approximately 10% anionic surfactant-sodium laureth sulfate, about 3% amphoteric surfactant-betaine, with 0.2% cationic conditioning polymer. 5% of either the inventive PO HIPE or the comparative PO Gel are added to the formulation. The full formulation is shown in Table 2. It should be noted that the comparative PO Gel needs to be melted first and combined with surfactants at higher temperature. No such step is required for the inventive PO HIPE. Melting of the additive is not a desirable procedure for making body wash formulation, but is used in this example in order to allow for collection of the comparative data.

Body Wash Sensory Feel Test Protocol

1. Panelists wash both hands and forearms with commercial Ivory bar soap.
2. Dry hands and forearms.
3. Using a syringe, place 0.5 ml of body wash onto the panelist's left hand.
4. Add 2.5 ml of tap water onto the panelist's left hand. Panelist lathers the body wash 10 times.
5. Add another 2.5 ml of tap water onto the panelist's left hand and lather the body wash for 20 seconds.
6. Rate Foam Volume 1-10. Higher scale means high amount of foam volume, which is highly desirable in rinse-off application.
7. Rate Foam Feel on Hands 1-10.
8. Panelist places all foam into right hand and places it on left forearm with a few gentle strokes.
9. Rate Foam Feel on Forearm 1-10.
10. Panelist washes both hands. Then, forearm is placed under running tap water until soap is gone (have the timer on to make note of the time it takes to clean off the body wash).
11. Panelist feels forearm and rates wet feel from 1 to 10.
12. Pat dry.
13. Wash hands again with Ivory bar soap. NOT FOREARMS. Dry hands.
14. Process is repeated with forearms reversed with remaining formulation (test substance or control). Panelist places all foam into left hand and places it on right forearm with a few gentle strokes.
15. After air drying of forearm, panelist rates dry feel, moisturization, smoothness and softness (1 to 10). Record comments Higher scales mean better performance, such as higher amount of foam volume, creamier foam, and smoother/better moisturizing feel.

Results and Discussion. Table 3 below provides the panel results from comparing inventive PO HIPE against comparative PO Gel in a generic rinse-off body wash formulation. The data shows that inventive PO HIPE can deliver creamier foam during the washing process and it also provides a better smooth and moisturizing feel after skin is immediately dry and after 30 min dry period, which means it can provide a longer smooth feel. This is quite desirable for consumers. On the other hand, the foam volume and the feel during wash (wet feel) are the same for PO HIPE and PO Gel.

TABLE 2

| Ingredients | INCI | PO Gel (w/w %) (Comparative) | 5% PO HIPE (w/w %) (Inventive) |
|---|---|---|---|
| DI Water | Water | q.s. to 100 | q.s. to 100 |
| Sodium Laureth Sulfate (1EO, 25% Active) | Sodium Laureth Sulfate | 40.00 | 40.00 |
| Cocamidopropyl Betaine | Cocamidopropyl Betaine | 10.00 | 10.00 |
| Guar Hydroxypropyltrimonium Chloride (a conditioning polymer) | Guar Hydroxypropyltrimonium Chloride | 0.10 | 0.10 |
| PO Gel (comparative) | — | 5.00 | |
| PO HIPE (inventive | — | | 5.00 |
| Acrylates Copolymer | Acrylates Copolymer (a thickener) | 7.00 | 7.00 |
| Fragrance | | 2.00 | 2.00 |
| TEA (pH adjuster) | Triethanolamine | adjust pH 5.5~6.0 | adjust pH 5.5~6.0 |
| Preservatives | | q.s. | q.s. |

TABLE 3

| Sample | 5% PO Gel (comparative) | 5% PO HIPE (inventive) |
|---|---|---|
| Foam Volume | 4.0 | 4.0 |
| Foam Feel: Hands | 5.0 | 5.0 |
| Foam Feel: Forearm | 4.5 | 6.0 |
| Feel of Skin after Rinsing/Wet | 6.0 | 5.5 |
| Feel of Skin after Drying Off (Initial) | 6.0 | 8.0 |
| Feel of Skin after Drying Off (30 mins) | 6.5 | 8.0 |

Example 6. Comparison of Inventive PO HIPE Versus Control

In this example, PO HIPE from Example 1 is compared against a control in a body wash formulation. The control body wash formulation contains the same ingredients except for the PO HIPE. The body wash formulation is shown in Table 4.

TABLE 4

| Ingredients | INCI | Control (w/w %) (Comparative) | 5% PO HIPE (w/w %) (Inventive) |
|---|---|---|---|
| DI Water | Water | q.s. to 100 | q.s. to 100 |
| Sodium Laureth Sulfate (1EO, 25% Active) | Sodium Laureth Sulfate | 40.00 | 40.00 |
| Cocamidopropyl Betaine | Cocamidopropyl Betaine | 10.00 | 10.00 |
| Guar Hydroxypropyltrimonium Chloride | Guar Hydroxypropyltrimonium Chloride | 0.10 | 0.10 |
| PO HIPE | — | | 5.00 |
| Acrylates Copolymer | Acrylates Copolymer | 10.00 | 10.00 |
| Fragrance | | 2.00 | 2.00 |
| TEA | | adjust pH 5.5~6.0 | adjust pH 5.5~6.0 |
| Preservatives | | q.s. | q.s. |
| Viscosity(cPs) | | 18,446 | 10,448 |

Results and Discussion. Table 5 below provides the data comparing inventive PO HIPE against the control in a generic rinse-off body wash formulation. The data shows that the inventive PO HIPE can deliver greater improvement on after-feel at 0 min and 30 min dry, and deliver better creamier foam feel than the control formulation.

TABLE 5

| PO HIPE vs. Control | | |
|---|---|---|
| Sample | Control (comparative) | 5% PO HIPE (inventive) |
| Foam Volume | 6.0 | 4.5 |
| Foam Feel: Hands | 6.0 | 6.8 |
| Foam Feel: Forearm | 6.5 | 7.2 |
| Feel of Skin after Rinsing/Wet | 3.8 | 4.5 |
| Feel of Skin after Drying (0 min) | 5.5 | 7.5 |
| Feel of Skin after Drying (30 min) | 3.5 | 5.5 |

In summary, concentrated emulsions of the invention can be easily formulated into personal care compositions, such as aqueous rinse-off skin care formulations. Moreover, and the inventive emulsions, when incorporated in a personal care composition, can deliver a better smooth/moisturizing skin feel.

What is claimed is:

1. A personal care composition comprising:

a personal care additive, wherein the personal care additive is a skin care active selected from the group consisting of sunscreens, skin colorants, drug substances, anti-oxidants, anti-aging ingredients, vitamins, natural extracts, skin protectants, conditioners, moisturizers, humectants and ultraviolet radiation absorbers: and a concentrated emulsion comprising:

(a) from 60 to 95 wt %, based on the total weight of the emulsion, of an internal phase comprising:

(i) a low density polyolefin with a density equal to or below 0.90 g/cm$^3$, and (ii) a cosmetically acceptable solvent;

(b) from 0.1 to 30 wt %, based on the total weight of the emulsion, of a surfactant; and (c) balance water as a continuous phase, wherein the internal phase further comprises a high density polyolefin with a density above 0.90 g/cm$^3$, and wherein the high and low density polyolefins have an average melt index greater than 7.

2. The personal care composition of claim 1, wherein the low density polyolefin contains one or more functional groups.

3. The personal care composition of claim 1, wherein the cosmetically acceptable solvent comprises a hydrocarbon solvent, an ester solvent, a silicone oil solvent, or a mixture of two or more thereof.

4. The personal care composition of claim 1, wherein the cosmetically acceptable solvent is a $C_{14}$-$C_{22}$ hydrocarbon oil.

5. The personal care composition of claim 1, wherein the internal phase comprises: from 0 to 30 wt % of a high density polyolefin, from 5 to 30 wt % of the low density polyolefin, and balance the cosmetically acceptable solvent, each based on the total weight of the internal phase.

6. The personal care composition of claim 1, wherein the personal care additive comprises one or more of: an emollient, an emulsifier, a surfactant, a thickener, or a sunscreen.

7. The personal care composition of claim 1, wherein the personal care composition is a rinse-off personal care composition.

8. A method of making a personal care of claim 1, the method comprising: adding the polyolefin blend to the personal care composition in the form of a concentrated emulsion.

9. A personal care composition comprising:

a personal care additive, wherein the personal additive is a sunscreen selected from the group consisting of para aminobenzoic acid, avobenzone, cinoxate, dioxybenzone, homosalate, menthyl anthranilate, octocrylene, octyl methoxycinnamate, octyl salicylate, oxybenzone, padimate O, phenylbenzimidazole sulfonic acid, sulisobenzone, trolamine salicylate, titanium dioxide, zinc oxide, benzophenones, 20 benzylidenes, salicylates, diethanolamine methoxycinnamate, digalloy trioleate, ethyl dihydroxypropyl PABA, glyceryl aminobenzoate, and lawsone with dihydroxy acetone and red petrolatum;

a concentrated emulsion comprising:

(a) from 60 to 95 wt %, based on the total weight of the emulsion, of an internal phase comprising:

(i) a low density polyolefin with a density equal to or below 0.90 g/cm$^3$, and (ii) a cosmetically acceptable solvent;

(b) from 0.1 to 30 wt %, based on the total weight of the emulsion, of a surfactant; and (c) balance water as a continuous phase, wherein the internal phase further comprises a high density polyolefin with a density above 0.90 g/cm$^3$, and wherein the high and low density polyolefins have an average melt index greater than 7.

* * * * *